United States Patent [19]
Kato et al.

[11] Patent Number: 4,909,922
[45] Date of Patent: Mar. 20, 1990

[54] HEATER-BUILT-IN OXYGEN SENSOR

[75] Inventors: Nobuhide Kato, Aichi; Yasuhiko Hamada, Nagoya, both of Japan

[73] Assignee: NGK Insulators, Ltd., Nagoya, Japan

[21] Appl. No.: 359,269

[22] Filed: May 31, 1989

[30] Foreign Application Priority Data

Jun. 2, 1988 [JP] Japan .................. 63-136269

[51] Int. Cl.$^4$ ............................................. G01N 27/58
[52] U.S. Cl. ..................................... 204/406; 204/425
[58] Field of Search ............... 204/406, 425, 426, 427, 204/428, 429, 1 S

[56] References Cited

U.S. PATENT DOCUMENTS

| 4,345,985 | 8/1982 | Tohda et al. ............... 204/425 X |
| 4,419,213 | 12/1983 | Oshima et al. ............... 204/425 |
| 4,462,890 | 7/1984 | Touda et al. ............... 204/425 |
| 4,559,126 | 12/1985 | Mase et al. ............... 204/425 |
| 4,629,549 | 12/1986 | Kojima et al. ............... 254/406 |
| 4,784,743 | 11/1988 | Iino et al. ............... 204/425 |
| 4,798,693 | 1/1989 | Mase et al. ............... 264/44 |
| 4,814,059 | 3/1989 | Nishizawa et al. ............... 204/406 |
| 4,839,019 | 6/1989 | Takahama et al. ............... 204/425 |

FOREIGN PATENT DOCUMENTS 54-140145 10/1979 Japan .
54-164191 12/1979 Japan .
55-30681 3/1980 Japan .
57-142555 9/1982 Japan .
57-192848 11/1982 Japan .
61-134656 6/1986 Japan .
61-137055 6/1986 Japan .
62-10660 1/1987 Japan .
62-214347 9/1987 Japan .

Primary Examiner—G. L. Kaplan
Attorney, Agent, or Firm—Arnold, White & Durkee

[57] ABSTRACT

A heater-built-in oxygen sensor having an electrochemical cell, a reservoir formed in substantial communication with a reference electrode of the cell, an electrically insulating member held in communication with the reservoir, a heating element disposed in contact with the insulating member, and cooperating with the cell and insulating member to constitute a major portion of an oxygen sensing element, and a direct current power source which is located outside the sensing element and to which the heating element is electrically connected. The low-potential portion of the sensing element connected to the negative terminal of the power source is electrically connected to a measuring electrode of the cell, so that a leak current of at least 0.1 microampere flows from the high-potential portion of the heating element connected to the positive terminal of the power source, to the insulating member through the insulating layer, at an elevated operating temperature of the sensing element, whereby oxygen is pumped from the external measurement gas to which the measuring electrode is exposed, into the reservoir as a reference gas to which the reference electrode is exposed. The reservoir may be defined by a porous structure of the insulating member.

17 Claims, 5 Drawing Sheets

HEATER-BUILT-IN OXYGEN SENSOR

BACKGROUND OF THE INVENTION

1. Field of the Invention

The present invention relates in general to a heater-built-in oxygen sensor, and more particularly to an oxygen sensor with improved operating reliability, which incorporates electric heating means for generating heat to maintain a desired operating temperature of an electrochemical cell which produces an electromotive force due to a difference in oxygen concentration between a measurement gas and a reference gas.

2. Discussion of the Prior Art

In the field of controlling the air/fuel ratio of an air-fuel mixture to be supplied to an internal combustion engine used for a motor vehicle, for example, it is known to use an oxygen sensor which utilizes an oxygen-ion conductive solid electrolyte material such as a zirconia ceramic, for detecting the oxygen concentration of exhaust gases emitted from the engine, according to the principle of an oxygen concentration cell.

Such an oxygen sensor for determining the oxygen concentration has a sensing element which includes a planar, columnar, tubular or otherwise shaped solid electrolyte body, and electrodes formed on the inner and outer surfaces of the solid electrolyte body. More specifically, the electrode on the inner surface of the solid electrolyte body is exposed to the ambient atmosphere, so as to serve as a reference electrode, while the electrode on the outer surface of the solid electrolyte body is exposed to an exhaust gas to be measured (measurement gas). An electromotive force is induced between the reference and measuring electrodes, due to a difference in oxygen concentration between the ambient atmosphere and the exhaust gas. The induced electromotive force is applied to a suitable measuring apparatus, to determine the oxygen concentration of the exhaust gas.

To assure accurate and reliable operation of the oxygen sensor even when the temperature of the exhaust gas is relatively low, a suitable heater or heating means is generally provided to heat at least the oxygen detecting portion of the sensing element on which the electrodes are disposed, so that the oxygen detecting portion is maintained at a desired elevated operating temperature. For example, an electric resistance rod heater is disposed in a bore formed in a tubular sensing element, as disclosed in laid-open Publication No. 57-142555 of unexamined Patent Application. Alternatively, an electric resistance heating element is embedded in a laminar structure of a planar sensing element, as disclosed in laid-open Publication No. 54-140145.

In the oxygen sensor as described above, the measuring electrode formed on the outer surface of the oxygen detecting distal portion of the sensing element is exposed to the measurement gas in the external space, while the reference electrode formed in the inner surface of the oxygen detecting portion communicates with a suitable reference gas passage which is formed through the sensing element, so as to extend from the proximal end portion to the oxygen detecting distal portion. This reference gas passage is open at the proximal end of the sensing element, so that the ambient air is introduced into the passage as a reference gas to which the reference electrode is exposed. Usually, the sensing element is accommodated in a suitable metallic covering member which has an air inlet through which the ambient air flows for introduction into the reference gas passage.

When the oxygen sensor of the type indicated just above is exposed to water or moisture, the sensing element may be adversely influenced by such water or moisture which is introduced into the covering member through the air inlet. For instance, the electrical insulation of the sensing element is deteriorated, causing inaccurate output signals of the sensor, or the oxygen partial pressure of the reference gas in the reference gas passage is lowered due to evaporation of the introduced water or moisture, whereby the output signals do not accurately reflect the oxygen concentration of the measurement gas. Further, the ceramic materials of the sensing element may be physically damaged due to exposure to the water or moisture.

In view of the above problem, laid-open Publication No. 62-214347 proposes providing an oxygen sensing element with exclusive oxygen pumping means for performing an oxygen pumping action to produce a reference atmosphere (having the predetermined or reference oxygen concentration) within an enclosed space formed in the sensing element. The provision of such oxygen pumping means necessarily increases the number of fabrication process steps and the constructional complexity of the sensor, which may result in increasing the rejection ratio during manufacture of the sensor. There is proposed an alternative solution the above problem, wherein the electrochemical cell having the measuring and reference electrodes is also utilized as the oxygen pumping means. That is, a pumping current is applied through a resistor to the measuring and reference electrodes. However, the provision of the resistor also increases the number of process steps of the sensing element. Where the resistor is incorporated within the sensing element, the resistor suffers from relatively low heat resistance.

SUMMARY OF THE INVENTION

It is therefore an object of the present invention to provide an oxygen sensor with built-in electric heating means, which is reliable in operation, easy to manufacture with a comparatively small number of process steps, and simple in construction and highly water-tight without a need of communication with the ambient atmosphere as a reference gas.

The above object may be attained according to a first aspect of the present invention, which provides a heater-built-in oxygen sensor, comprising: (a) an electrochemical cell having an oxygen-ion conductive solid electrolyte body, and a measuring electrode and a reference electrode which are formed on the solid electrolyte body and are exposed to a measurement gas and a reference gas, respectively, the cell being operated such that an electromotive force is induced between the measuring and reference electrodes according to a difference in oxygen concentration between the measurement and reference gases; (b) an electrically insulating member which includes a porous structure held in contact with the reference electrode; (c) a heating element disposed in contact with the electrically insulating member, and cooperating with the cell and the insulating member to constitute a major portion of a sensing element; and (d) a direct current power source which is disposed outside the sensing element and to which the heating element is electrically connected. The heating element has a low-potential portion and a high-potential portion which are conducted to a negative terminal and a positive terminal of the power source, respectively. The low-potential portion of the heating element is electrically connected to the measuring electrode, so that a leak current of at least 0.1 microampere flows from the high-potential portion through the insulating member to the measuring electrode at an elevated operating temperature of the sensing element, whereby oxygen is pumped from the measurement gas into the porous structure of the insulating member as the reference gas.

The above object may also be attained according to a second aspect of the invention, which provides a heater-built-in oxygen sensor, comprising: (a) an electrochemical cell having an oxygen-ion conductive solid electrolyte body, and a measuring electrode and a reference electrode which are formed on the solid electrolyte body and are exposed to a measurement gas and a reference gas, respectively, the cell being operated such that an electromotive force is induced between the measuring and reference electrodes according to a difference in oxygen concentration between the measurement and reference gases; (b) a reservoir formed in substantial communication with the reference electrode, for storing the reference gas; (c) an electrically insulating member held in communication with the reservoir; (d) a heating element disposed in contact with the electrically insulating member, and cooperating with the cell and the insulating member to constitute a major portion of a sensing element; (e) a direct current power source which is disposed outside the sensing element and to which the heating element is electrically connected. The heating element has a low-potential portion and a high-potential portion which are connected to a negative terminal and a positive terminal of the power source, respectively. The low-potential portion of the heating element is electrically connected to the measuring electrode, so that a leak current of at least 0.1 microampere flows from the high-potential portion through the insulating member to the measuring electrode, at an elevated operating temperature of the sensing element, whereby oxygen is pumped from the measurement gas into the reservoir as the reference gas.

The above object may also be attained according to a third aspect of the invention, which is different from the second aspect of the invention, in connection with the relationship among the reference electrode, electrically insulating member and reservoir. Namely, the electrically insulating member has a porous structure which is held in communication with one of opposite major surfaces of said reference electrode which is remote from said measuring electrode, and the reservoir is formed and disposed such that the reservoir is held in substantial communication with said electrically insulating member, for storing said reference gas.

The object of the invention may also be attained according a fourth aspect of the invention, which is different from the above second and third aspects of the invention, in connection with the relationship among the reference electrode, electrically insulating member and reservoir. That is, the electrically insulating member is disposed in communication with one of opposite major surfaces of said reference electrode which is remote from said measuring electrode, while the reservoir is formed and disposed such that the reservoir is held in communication with the other of said opposite surfaces of said reference electrode, for storing said reference gas.

In the oxygen sensor of the present invention constructed as described above, a portion of the electric current applied to the heating element leaks from the high-potential portion of the heating element toward the measuring electrode, whereby oxygen in the measurement gas is captured by the measuring electrode, transferred toward the high-potential portion of the heating element, and stored in the porous structure of the electrically insulating member according to the above-described one aspect of the invention, or in the reservoir according to the second, third and fourth aspects of the invention. Since the reference electrode is in substantial communication with the porous structure of the insulating layer or the reservoir, the reference electrode contacts the oxygen stored as the reference gas in the porous structure of the insulating member or in the reservoir. Consequently, an electromotive force is induced between the measuring and reference electrodes, according to a difference in oxygen concentration between the external measurement gas and the reference gas. Thus, the oxygen concentration of the measurement gas may be detected or determined.

It will be understood that the oxygen sensor constructed according to the invention does not have a reference air passage for communication of the reference electrode with the ambient air, which is used as the reference gas. Accordingly, the sensor can be constructed with high fluid-tightness. Further, the present sensor is capable of pumping the oxygen from the external measurement gas into the sensing element, by simply connecting the low-potential portion of the heating element to the measuring electrode. That is, the sensor does not require exclusively designed oxygen pumping means, and can therefore be simplified in construction and fabricated in comparatively reduced number of process steps, while assuring accurate and reliable detection or determination of the oxygen concentration of the measurement gas.

Preferably, the low-potential portion of the heating element and the measuring electrode are electrically connected at a location within the sensing element or on a surface of the sensing element.

In the sensor according to each of the four aspects of the invention, the electrically insulating member may consist of a first insulating layer in contact with the reference electrode, and a second insulating layer which cooperates with the first insulating layer to form an electrically insulating mass in which the heating element is embedded.

The heating element may consist of a heat-generating element, and a pair of electrical lead portions which are connected to the negative and positive terminals of the direct current power source and which provide the low-potential and high-potential portions, respectively.

In the sensor according to the invention, the electrically insulaing member is preferably a porous structure, so that the pumped-in oxygen may easily flow into the reservoir.

Where the reservoir is provided according to the second aspect ov the invention, the sensormay comprise a solid electrolyte spacer layer interposed between the solid electrolyte body of the electrochemical cell and the electrically insulating member, so that the reservoir is defined by a hole or void formed through the spacer layer such that the opposite open ends of the hole are closed by the reference electrode and the insulating layer. In this case, the reference electrode may have a surface area which is larger than a cross sectional area of the reservoir in a plane parallel to a plane of the reference electrode. In this instance, it is desirable that the surface of the reference electrode on the side of the reservoir is covered by a porous ceramic layer.

Alternatively, the reservoir may be provided in the form of an array of holes which are formed through the spacer layer in communication with the reference electrode.

BRIEF DESCRIPTION OF THE DRAWINGS

The foregoing and optional objects, features and advantages of the present invention will become more apparent by reading the following detailed description of presently preferred embodiments of the invention, when considered in connection with the accompanying drawings, in which.

DETAILED DESCRIPTION OF THE PREFERRED EMBODIMENTS

Figure 1:
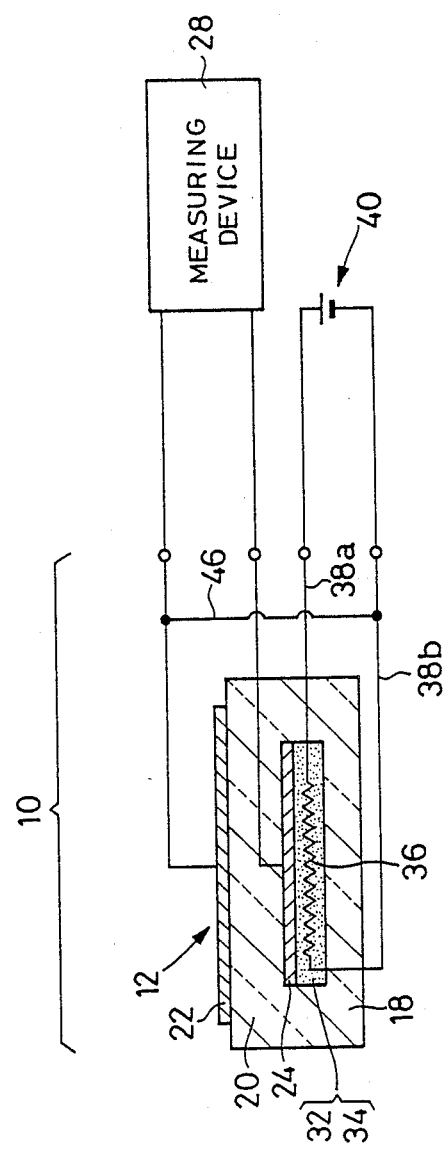
FIG. 1 is a schematic view of one embodiment of a heater-built-in oxygen sensor of the invention, showing a distal oxygen detecting portion of its oxygen sensing element in transverse cross section.
Figure 2:
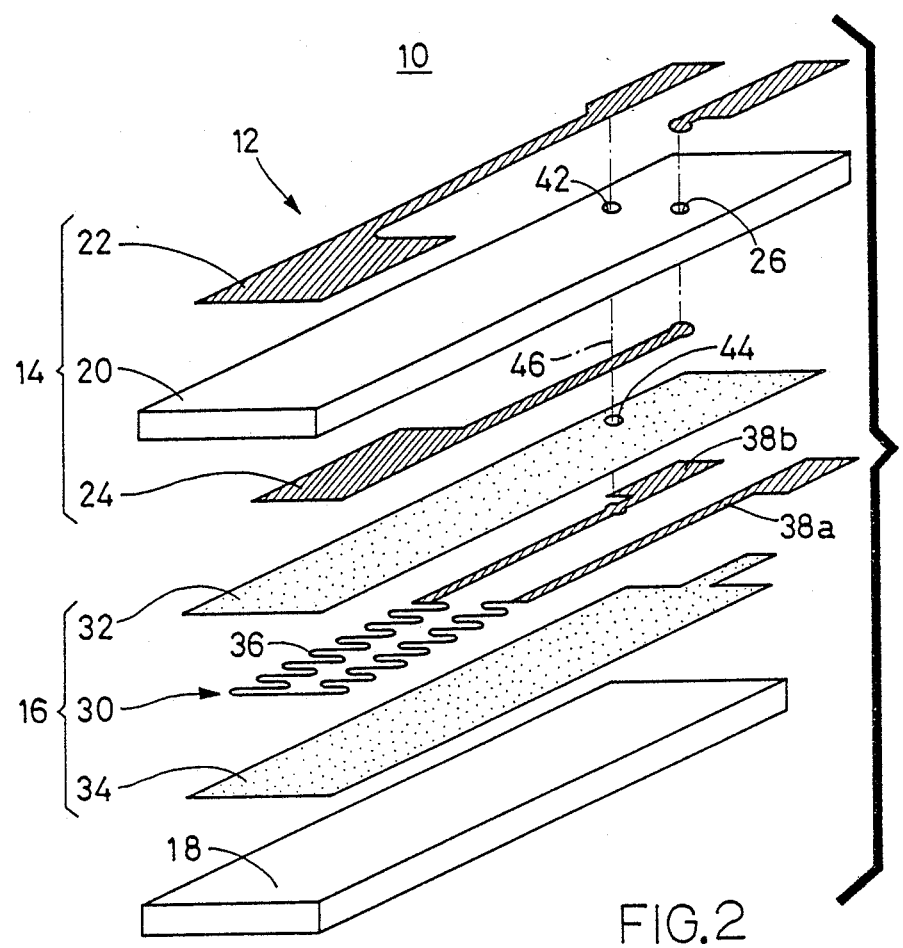
FIG. 2 is a schematic exploded perspective view of the oxygen sensin element of the sensor of FIG. 1.

Referring first to the schematic views of FIGS. 1 and 2, reference numeral 10 denotes an oxygen sensing element which has an integrally fired, generally elongate planar laminar structure. The sensing element 10 includes a distal oxygen detecting portion 12 for detecting the concentration of oxygen in a gaseous fluid to be measured, according to the principle of an oxygen concentration cell. The oxygen detecting portion 12 is a left-hand side end portion of the sensing element 10, as seen in FIG. 2. This distal portion 12 cooperates with a right-hand side proximal portion as seen in the same figure, to constitute the sensing element 10. The proximal portion has electrical leads for obtaining electric signals from electrodes 22, 24 (which will be described) of the oxygen detecting portion 12, and electrical lead portions 38a, 38b of a heating element 30 (which will be described). The laminar structure of the sensing element 10 consists of an electrochemical cell 14 (including the electrodes 22, 24), a heater layer 16 (including the heating element 30), and a substrate 18 on which the electrochemical cell 14 and the heater layer 16 are superposed. The substrate 18 is made of a solid electrolyte material which is the same as a solid electrolyte body 20 of the electrochemical cell 14.

The solid electrolyte body 20 of the electrochemical cell 14 of the sensing element 10 is a planar body formed of a suitable solid electrolyte material such as stabilized zirconia, which exhibits oxygen-ion conductivity at an elevated temperature. The solid electrolyte body 20 has the measuring electrode 22 formed on its outer major surface so that the measuring electrode 22 is exposed to the external measurement fluid. This electrode 22 is made of a suitable known electrically conductive material such as platinum. On a portion of the inner major surface of the solid electrolyte body 20 which is opposite to the measuring electrode 22, there is formed the reference electrode 24 of an electrically conductive material similar to that of the measuring electrode 22. The reference electrode 24 has an electrical lead which extends to the outer surface of the solid electrolyte body 20, through a through-hole 26 formed through the body 20. The electrical lead of the reference electrode 24 further extends from the through-hole 26, and the electrical lead of the measuring electrode 22 extends, in the same plane on the outer surface of the solid electrolyte body 20, for electrical connection with a suitable external measuring device 28 such as a computer, so that an electromotive force induced between the two electrodes 22, 24 of the cell 14 is detected to determine the oxygen concentration.

The heating element 30 of the heater layer 16 superposed on the electrochemical cell 14 is sandwiched between a pair of electrically insulating layers 32, 34 each of which has a porous structure made of a suitable electrically insulating material such as alumina. In other words, the inner and outer insulating layers 32, 34 are superposed on each other to provide an integral ceramic insulating layer in which the heating element 30 is embedded. The heating element 30 consists of a heat-generating portion 36 aligned with the distal oxygen detecting portion 12 of the sensing element 10, and a pair of electrical lead portions 38a, 38b for connecting the heat-generating portion 36 to an external DC power source 40, for energizing the heat-generating portion 36 so that the portion 36 generates heat for heating the oxygen detecting portion 12. More specifically, the electrical lead portion 38a is connected to a positive terminal of the DC power source 40, while the electrical lead portion 38b is connected to a negative terminal of the power source 40. While a heater current is supplied from the power source 40 to the heat-generating element 36, the electrical lead portion 38a has a relatively high potential, and the electrical lead portion 38b has a relatively low potential. In this sense, the electrical portions 38a, 38b will be referred to as a high-potential and a low-potential portion, respectively, when appropriate.

The low-potential portion 38b of the heating element 30 which is connected to the DC power source 40 is electrically connected to the measuring electrode 22 (more precisely, the electrical lead of the electrode 22), through a conductor path 46 defined by through-holes 42 and 44 that are formed through the solid electrolyte body 20 and insulating layer 32.

The sensing element 10 constructed as described above may be fabricated in various known processes such as printing. For example, the unfired measuring and reference electrodes 22, 24 are formed by printing on the appropriate opposite major surfaces of the unfired solid electrolyte body. Then, the unfired inner insulating layer, unfired heater element 30 and unfired outer insulating layer 34 are sequentially superposed in this order by printing on the inner major surface of the unfired solid electrolyte body 20. The thus prepared unfired laminar body 20, 22, 24, 32, 30, 34 is superposed on the unfired substrate 18, and the obtained unfired laminar structure is fired into the fired sensing element 10.

In the present sensing element 10 in which the low-potential portion 38b of the heating element 30 is electrically connected to the measuring electrode 22, a portion of the heater current applied to the heating element 30 from the external DC power source 40 leaks from the high-potential portion 38a through the insulating layers 32, 34, due to reduction in the electrical resistance of the insulating layers 32, 34 at an elevated temperature thereof. As a result, the leak current flows toward the measuring electrode 22 through the solid electrolyte body 20, and flows from the measuring electrode 22 toward the low-potential portion 38b of the heating element 30, through the conductor path 46.

With a flow of the leak current from the high-potential portion 38a of the heating element 30 to the measuring electrode 22, the oxygen in the measurement gaseous fluid in the external space is capatured by the measuring electrode 22, and transferred as oxygen ions toward the high-potential portion 38a of the heating element 30. The oxygen ions transferred to the high-potential portion 38a are supplied as oxygen to the porous insulating layers 32, 34 in contact with the reference electrode 24. The oxygen is stored in the porous structure of the layers 32, 34, as a reference gas having a reference oxygen concentration, with which the reference electrode 24 communicates and contacts.

As described above, the leak current from the heating element 30 results in introducing oxygen from the external measurement gas into the sensing element 10, as the reference gas adjacent to or surrounding the reference electrode 24. Accordingly, it is not necessary to provide the sensing element 10 with a passage formed therethrough for introducing the ambient atmosphere, or an exclusive oxygen pumping cell for producing a reference gas within the sensing element. Without such a reference gas passage or an oxygen pumping cell, the instant sensing element 10 is capable of producing an electromotive force due to a difference in oxygen concentration between the external measurement gas and the reference gas adjacent to the reference electrode 24. Namely, the measuring electrode 22 of the electrochemical cell 14 is held in communication or contact with the external measurement gas, while the reference electrode 24 is held in communication with the reference gas having the reference oxygen concentration, which is produced by the leak current from the heating element 30. As a result, the difference in oxygen concentration between the external measurement gas and the internal reference gas is detected as an electromotive force induced between the two electrodes 22, 24. The signal indicative of the electromotive force is fed to the measuring device 28, and processed to determine the oxygen concentration of the measurement gas.

During the operation of the oxygen sensor described above, a consumed electric current flows from the positive terminal of the cell 14, i.e., from the reference electrode 24 through the measuring device 28 toward the measuring electrode 22. Since this current flows in the direction opposite to that of the leak current from the heating element 30 (high-potential portion 38a), the oxygen stored as the reference gas in the porous structure of the insulating layers 32, 34 is consumed. In view of this phenomenon, the thickness, surface area, purity, material and other factors of the insulating layer 32 or layers 32, 34 are suitably adjusted or determined so that the leak current from the heating element 30 is held 0.1 microampere or more. Usually, the internal impedance of the measuring device 28 such as a computer is 10M ohms, and the maximum electromotive force induced in the electrochemical cell 14 is 1 V. This means that the maximum amount of the consumed current is 0.1 microampere, and therefore the reference gas adjacent to the reference electrode 24 will not be wholly consumed, provided that the leak current is held to be at least 0.1 microampere. Even if the amount of the leak current is excessively large, the oxygen pressure in the porous structure of the insulating layers 32, 34 will not become excessively high, since the insulating layers 32, 34 are exposed at their ends on the corresponding exposed end face of the sensing element 10, i.e., communicate with the ambient atmosphere. Therefore, the sensing element 10 will not be damaged by an excessively high pressure of the reference gas in the insulating layers 32, 34.

While the insulating layers 32, 34 are formed of alumina in the present embodiment, these layers may be formed of other electrically insulating materials such as steatite, mullite or other ceramic insulating materials, and semiconductor oxides or oxygen-ion conductive materials having a high electrical resistance. Generally, the electrical resistance of these electrically insulating materials is lowered at an elevated temperature at which an electrochemical cell is operated for detecting oxygen concentration.

In the present embodiment, both of the inner and outer insulating layers 32, 34 are porous. However, it is desirable that at least the inner insulating layer 32 be a porous structure, for effectively functioning as a reservoir for storing oxygen which is pumped in as the reference gas by means of the leak current from the heating element 30. The porous structure of the inner insulating layer 32 is also desirable for moving the pumped-in reference gas toward the reference electrode 24.

Where the outer insulating layer 34 as well as the inner insulating layer 32 is porous as in the present embodiment, the volume of the reservoir for the reference gas is accordingly increased. In this case, it is preferred that the thickness of the inner insulating layer 32 is determined so as to establish the optimum amount of the leak current, while the thickness of the outer insulating layer 34 is determined so as to establish the desired volume of the reservoir.

Figure 3:
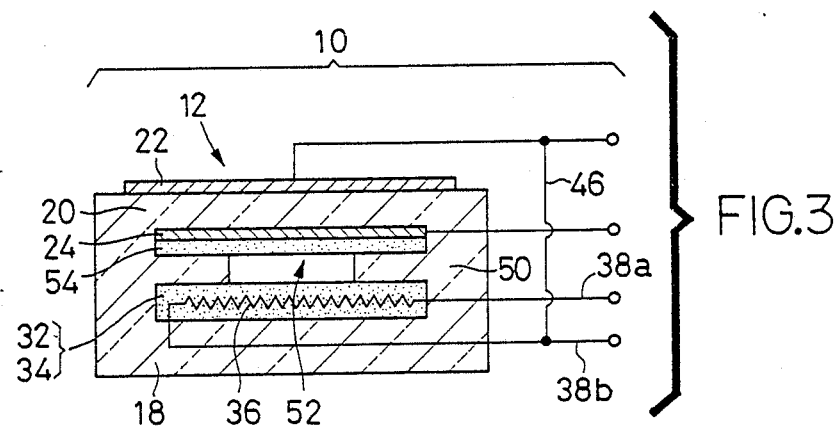
FIG. 3 is a schematic view corresponding to that of FIG. 1, illustrating another embodiment of the invention.
Figure 4:
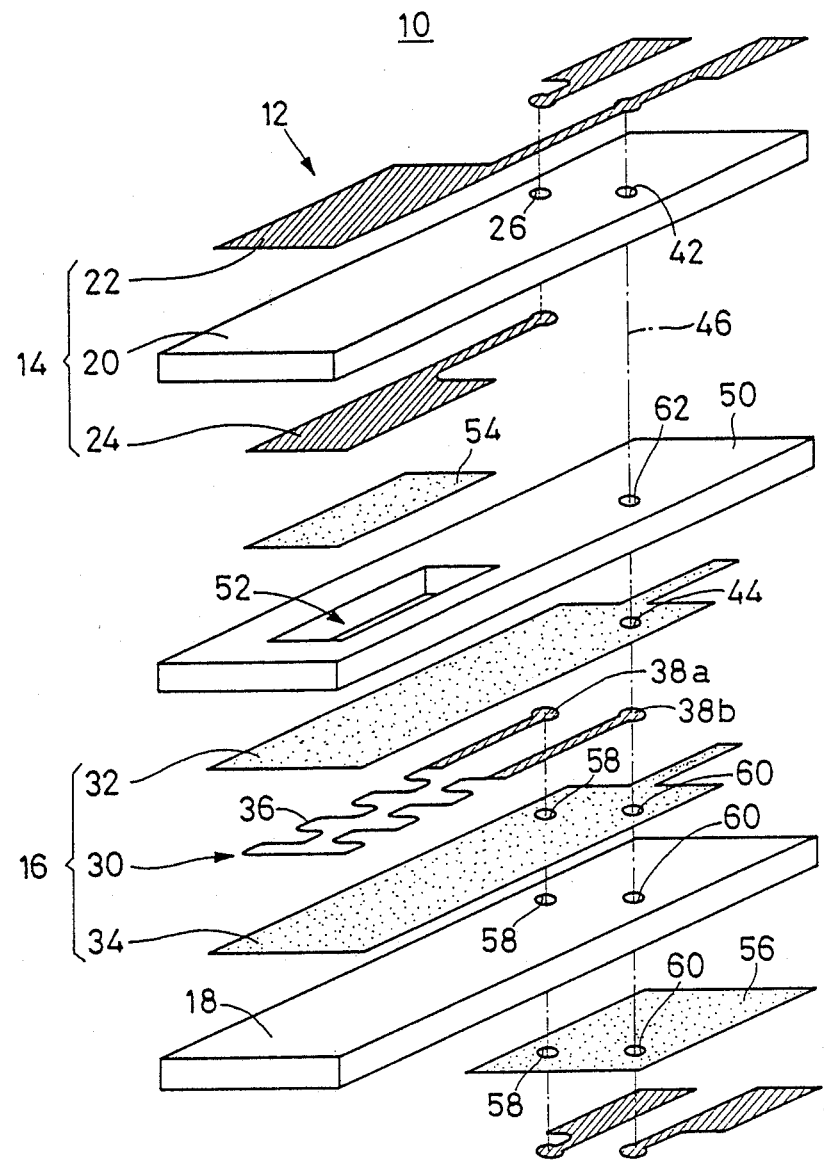
FIG. 4 is a schematic exploded perspective view of the sensing element of the sensor of FIG. 3, which corresponds to that of FIG. 2.

Referring next to FIGS. 3 and 4, there is shown a modified embodiment of the invention, in which a spacer layer 50 made of a material similar to that of the solid electrtolyte body 20 is interposed between the electrochemical cell 14 and the heater layer 16. The spacer layer 50 has an opening closed as an enclosed internal space 52, to which is exposed the corresponding portion of the inner insulating layer 32 of the heater layer 16. Further, the reference electrode 24 of the electrochemical cell 14 is exposed to the internal space 52, through a porous ceramic layer 54 made of alumina. In this arrangement, the reference electrode 24 communicates with the atmosphere within the internal space 52, through the porous alumina layer 54.

Since the internal space 52 communicates with the porous insulating layer 32, the space 52 also functions as a reservoir for storing the reference gas which is pumped in by means of the heater leak current. The oxygen in the internal space 52 may be used as reference oxygen for the reference electrode 24, even before or until the electrical resistance of the insulating layer 32 (insulating layers 32, 34) has been sufficiently lowered due to a rise in the operating temperature of the sensing element 10 after the starting of a cold engine which produces a cold exhaust gas to be measured by the oxygen sensor.

In this modified embodiment, the entire surface area of the reference electrode 24 is covered by the porous alumina layer 54 formed thereon. Therefore, the peripheral portions of the reference electrode 24 that are located outside the internal space 52 as viewed toward the plane of the electrode 24 can communicate with the reference gas within the space 52, through the porous structure of the alumina layer 54. In other words, the reference gas flows through the porous alumina layer 54 toward the portions of the reference electrode 24 which are positioned between the solid electrolyte body 20 and the spacer layer 50, as seen in the plane of FIG. 3. However, if the reference electrode 24 itself is porous enough to permit the reference gas to easily flow into its peripheral portions, the porous alumina layer 54 may be eliminated.

The size or volume of the internal space 52 as the reservoir for storing the reference oxygen is determined by the amount of consumption of the reference gas by the electrochemical cell 14, during an operating period of the sensing element 10 at a low temperature, e.g., immediately after the engine whose exhaust gas is measured is started. Described more specifically, while the temperature of the insulating layers 32, 34 is low, oxygen is not sufficiently pumped into the internal space 52 by the leak current from the heating element 30, since the electrical resistance of the insulating layers 32, 34 is high. Accordingly, the oxygen already stored in the space 52 is reduced or consumed until the operating temperature of the sensing element 10 becomes high enough to permit a sufficient amount of external oxygen to be pumped into the space 52 by the leak current through the insulating layers 32, 34.

In the present modified embodiment, the same reference numerals as used in the first embodiment are used to identify the functionally corresponding components, and no redundant description of these components will be provided. However, the electrical lead portions 38a, 38b (high-potential and low-potential portions) of the heating element 30 are connected to an external DC power source (not shown in FIGS. 3 and 4) as indicated at 40 in FIG. 1, through through-holes 58, 60 which are formed through the outer insulating layer 34, the substrate 18, and an insulating layer 56 which is made of alumina or other insulating material and formed on the outer surface of the substrate 18. The low-potential portion 38b of the heating element 30 is connected to the measuring electrode 22, through the conductor path 46 which is defined by the through-holes 42, 44 indicated above, and a through-hole 62 formed through the spacer layer 50.

Figure 5:
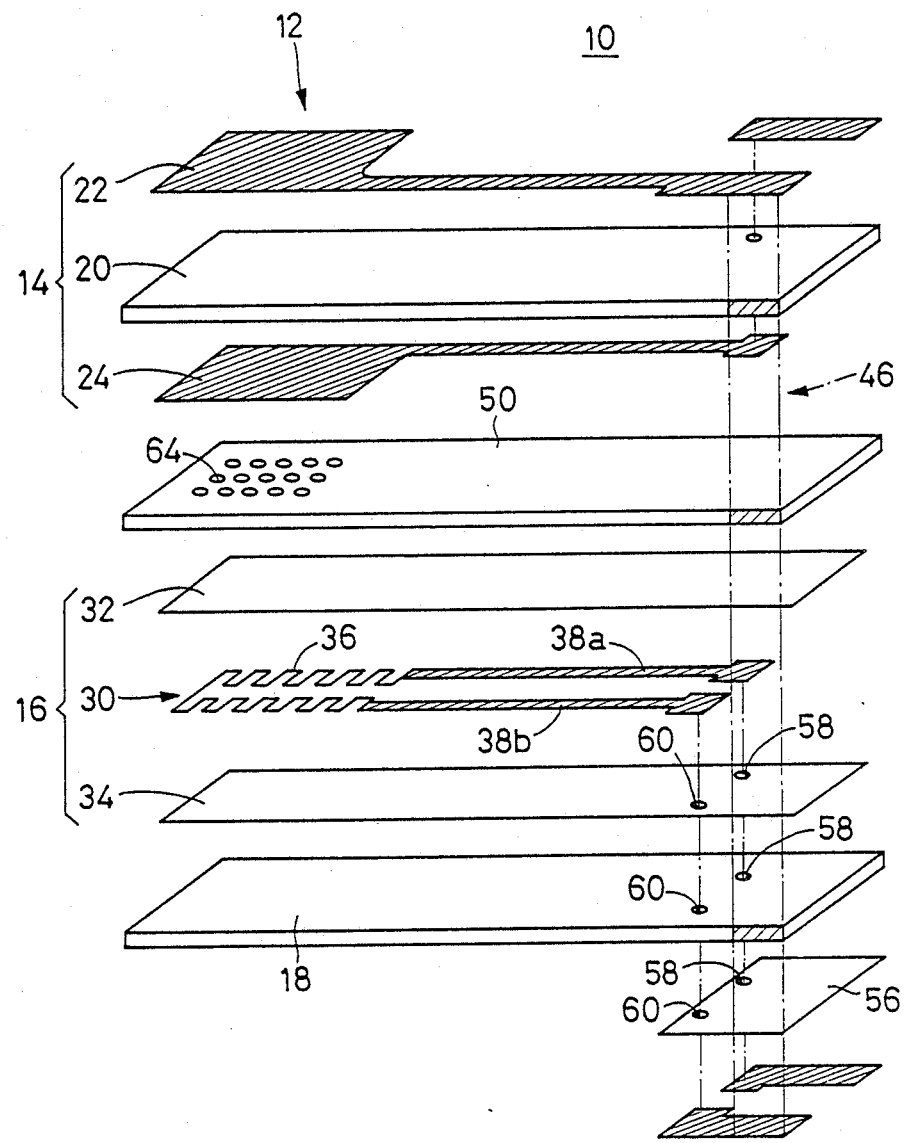
FIG. 5 is a schematic exploded perspective view of a further embodiment of the invention.

Referring to FIG. 5, there is shown a further modified embodiment of the invention, wherein the spacer layer 50 has an array of holes or apertures 64 which are formed therethrough and which have a relatively small diameter. These holes 64 are provided in place of the internal space 52, to function as the reservoir for the reference oxygen.

In the present modified embodiment, the electrical connection between the low-potential portion 38b of the heating element 30 and the measuring electrode 22 is effected by means of the conductor path 46 consisting of an electrical conductive material printed on a portion of one of the opposite long side surfaces of the sensing element 10, which is indicated by hatched lines in FIG. 5.

Figure 6:
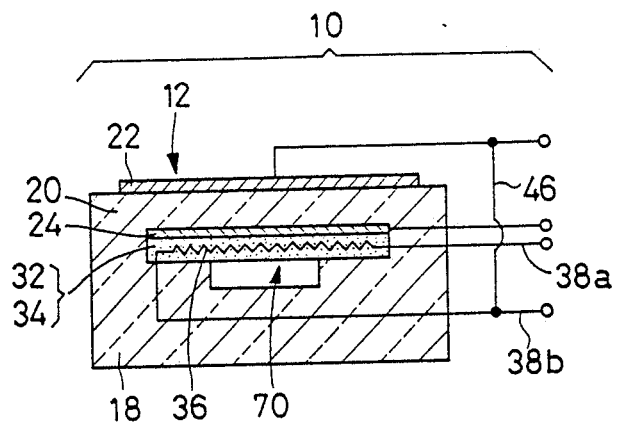
FIGS. 6 and 7 are views corresponding to that of FIG. 1, illustrating still further embodiments of the invention.
Figure 7:
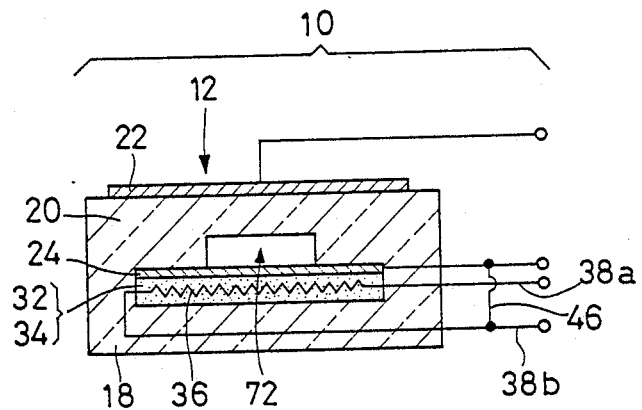

Referring to FIGS. 6 and 7, further modified embodiments of the invention will be described.

In the embodiment of FIG. 6, the electrically insulating layers 32, 34 are formed and disposed such that the layers are in contact and communication with the reference electrode 24, more precisely, with one of the opposite surfaces of the reference electrode 24 which is remote from the measuring electrode 22. Further, a reservoir 70 is formed and disposed in communication with the porous structure of the electrically insulating layers 32, 34. In this arrangement, too, the reference oxygen pumped into the sensing element 10 due to the leak heater current is stored in the reservoir 70.

In the embodiment of FIG. 7, too, the electrically insulating layers 32, 34 are formed and disposed in contact and communication with one of the opposite surfaces of the reference electrode 24 which is remote from the measuring electrode 22. However, the reference electrode 24 is held in direct communication with a reservoir 72 which is formed between the measuring and reference electrodes 22, 24. To permit a flow of the pump-in reference oxygen into the reservoir 72, the reference electrode 24 has a porous structure.

It will be understood that the electrical connection between the low-potential portion 38b and the measuring electrode 22 may be made by any suitable means other than the through-holes or the printed conductive material as used in the illustrated embodiments. While this electrical connection is preferably made within the sensing element 10 or on one of the outer surfaces of the sensing element 10, it can be made at a location outside the sensing element 10.

While the present invention has been described in its presently preferred embodiments, it is to be understood that the invention is not limited to the details of the illustrated embodiments, but the invention may be embodied with various changes, modifications and improvements, which may occur to those skilled in the art, without departing from the spirit and scope of the invention defined by the appended claims.

For example, the solid electrolyte body 20 of the electrochemical cell 14, whose major component preferably consists of stabilized zirconia ($ZrO_2$), may be formed of other oxygen-ion conductive solid electrolyte materials such as $SrCeO_3$, and a solid solution of $Bi_2O_3$ and oxides of rare earth.

It is desirable that the heating element 30 be formed of a material which is resistant to oxidation at an elevated temperature, for example, electrically conductive metals such as the platinum group metals including platinum, palladium, rhodium, iridium, ruthenium and osmium. For improving the adhesion of the heating element 30 to the insulating layers 32, 34, it is preferred that a finely divided ceramic powder be mixed with a powdered electrically conductive metal for the heating element 30.

While the sensing element 10 of the illustrated embodiments has a planar or plate-like configuration, the sensing element of the heater-built-in oxygen sensor according to the invention may take other shapes. For example, the sensing element may have a columnar or cylindrical shape prepared by a thick-film forming technique, as disclosed in laid-open Publication No. 61-272649 of unexamined Japanese Patent Application.

What is claimed is:
1. A heater-built-in oxygen sensor, comprising:
   an electrochemical cell having an oxygen-ion conductive solid electrolyte body, and a measuring electrode and a reference electrode which are formed on said solid electrolyte body and are ex- posed to a measurement gas and a reference gas, respectively, said cell being operated such that an electromotive force is induced between said measuring and reference electrodes according to a difference in oxygen concentration between said measurement and reference gases;

an electrically insulating member including a porous structure which is held in contact with said reference electrode;

a heating element disposed in contact with said electrically insulating member, and cooperating with said cell and said insulating member to constitute a major portion of a sensing element;

a direct current power source which is disposed outside said sensing element and to which said heating element is electrically connected;

said heating element having a low-potential portion and a high-potential portion which are connected to a negative terminal and a positive terminal of said power source, respectively; and said low-potential portion of said heating element being electrically connected to said measuring electrode, so that a leak current of at least 0.1 microampere flows from said high-potential portion through said insulating member to said measuring electrode, at an elevated operating temperature of the sensing element, whereby oxygen is pumped from said measurement gas into said porous structure of said insulating member as said reference gas.

2. An oxygen sensor according to claim 1, wherein said low-potential portion of said heating element and said measuring electrode are electrically connected within said sensing element or on a surface of said sensing element.

3. An oxygen sensor according to claim 1, wherein said insulating member comprises a first insulating layer in contact with said reference electrode, and a second insulating layer which cooperates with said first insulating layer to form an electrically insulating mass in which said heating element is embedded.

4. An oxygen sensor according to claim 3, wherein said first insulating layer consists of a porous structure.

5. An oxygen sensor according to claim 1, wherein said heating element consists of a heat-generating element, and a pair of electrical lead portions which are connected to sai negative and positive terminals of said direct current power source and which provide said low-potential and high-potential portions, respectively.

6. A heater-built-in oxygen sensor, comprising:

an electrochemical cell having an oxygen-ion conductive solid electrolyte body, and a measuring electrode and a reference electrode which are formed on said solid electrolyte body and are exposed to a measurement gas and a reference gas, respectively, said cell being operated such that an electromotive force is induced between said measuring and reference electrodes according to a difference in oxygen concentration between said measurement and reference gases;

a reservoir formed in substantial communication with said reference electrode, for storing said reference gas;

an electrically insulating member held in communication with said reservoir;

a heating element disposed in contact with said electrically insulating member, and cooperating with said cell and said insulating member to constitute a major portion of a sensing element;

a direct current power source which is disposed outside said sensing element and to which said heating element is electrically connected;

said heating element having a low-potential portion and a high-potential portion which are connected to a negative terminal and a positive terminal of said power source, respectively; and said low-potential portion of said heating element being electrically connected to said measuring electrode, so that a leak current of at least 0.1 microampere flows from said high-potential portion through said insulating member to said measuring electrode, at an elevated operating temperature of the sensing element, whereby oxygen is pumped from said measurement gas into said reservoir as said reference gas.

7. An oxygen sensor according to claim 6, wherein said low-potential portion of said heating element and said measuring electrode are electrically connected within said sensing element or on a surface of said sensing element.

8. An oxygen sensor according to claim 6, wherein said electrically insulating member has a porous structure.

9. An oxygen sensor according to claim 6, wherein said insulating member comprises a first insulating layer held in communication with said reservoir, and a second insulating layer which cooperates with said first insulating ayer to form an electrically insulating mass in which said heating element is embedded.

10. An oxygen sensor according to claim 9, wherein said first insulating layer consists of a porous structure.

11. An oxygen sensor according to claim 6, wherein said heating element consists of a heat-generating element, and a pair of electrical lead portions which are connected to said negative and positive terminals of said direct current power source and which provide said low-potential and high-potential portions, respectively.

12. An oxygen sensor according to claim 6, further comprising a solid electrolyte spacer layer interposed between said solid electrolyte body of said electrochemical cell and said electrically insulating member, said reservoir being defined by said reference electrode, said spacer layer and said insulating layer.

13. An oxygen sensor according to claim 12, wherein said reference electrode has a surface area which is larger than a cross sectional area of said reservoir in a plane parallel to a plane of the reference electrode.

14. An oxygen sensor according to claim 13, wherein a surface of said reference electrode on the side of said reservoir is covered by a porous ceramic layer.

15. An oxygen sensor according to claim 6, further comprising a solid electrolyte spacer layer interposed between said solid electrolyte body of said electrochemical cell and said electrically insulating member, said reservoir consisting of an array of holes formed through said spacer layer in communication with said reference electrode.

16. A heater-built-in oxygen sensor, comprising:

an electrochemical cell having an oxygen-ion conductive solid electrolyte body, and a measuring electrode and a reference electrode which are formed on said solid electrolyte body and are exposed to a measurement gas and a reference gas, respectively, said cell being operated such that an electromotive force is induced between said measuring and reference electrodes according to a difference in oxygen concentration between said measurement and reference gases;

an electrically insulating member including a porous structure which is held in communication with one of opposite major surfaces of said reference electrode which is remote from said measuring electrode;

a reservoir formed in substantial communication with said electrically insulating member, for storing said reference gas;

a heating element disposed in contact with said electrically insulating member, and cooperating with said cell and said insulating member to constitute a major portion of a sensing element;

a direct current power source which is disposed outside said sensing element and to which said heating element is electrically connected;

said heating element having a low-potential portion and a high-potential portion which are connected to a negative terminal and a positive terminal of said power source, respectively; and said low-potential portion of said heating element being electrically connected to said measuring electrode, so that a leak current of at least 0.1 microampere flows from said high-potential portion through said insulating member to said measuring electrode, at an elevated operating temperature of the sensing element, whereby oxygen is pumped from said measurement gas into said reservoir as said reference gas.

17. A heater-built-in oxygen sensor, comprising:

an electrochemical cell having an oxygen-ion conductive solid electrolyte body, and a measuring electrode and a reference electrode which are formed on said solid electrolyte body and are exposed to a measurement gas and a reference gas, respectively, said cell being operated such that an electromotive force is induced between said measuring and reference electrodes according to a difference in oxygen concentration between said measurement and reference gases;

an electrically insulating member held in communication with one of opposite major surfaces of said reference electrode which is remote from said measuring electrode;

a reservoir formed in communication with the other of said opposite surfaces of said reference electrode, for storing said reference gas;

a heating element disposed in contact with said electrically insulating member, and cooperating with said cell and said insulating member to constitute a major portion of a sensing element;

a direct current power source which is disposed outside said sensing element and to which said heating element is electrically connected;

said heating element having a low-potential portion and a high-potential portion which are connected to a negative terminal and a positive terminal of said power source, respectively; and said low-potential portion of said heating element being electrically connected to said measuring electrode, so that a leak current of at least 0.1 microampere flows from said high-potential portion through said insulating member to said measuring electrode, at an elevated operating temperature of the sensing element, whereby oxygen is pumped from said measurement gas into said reservoir as said reference gas.

* * * * *